US010996171B2

United States Patent
Hu (10) Patent No.: US 10,996,171 B2
(45) Date of Patent: May 4, 2021

(54) METHOD FOR DEVELOPING AND EXTRACTING BIOLOGICAL TRACE EVIDENCE

(71) Applicant: SUZHOU XIAOSONG SCIENCE & TECHNOLOGY DEVELOPMENT CO., LTD, Suzhou (CN)

(72) Inventor: Xiaosong Hu, Suzhou (CN)

(73) Assignee: SUZHOU XIAOSONG SCIENCE & TECHNOLOGY DEVELOPMENT CO., LTD, Suzhou (CN)

( * ) Notice: Subject to any disclaimer, the term of this patent is extended or adjusted under 35 U.S.C. 154(b) by 119 days.

(21) Appl. No.: 16/479,705

(22) PCT Filed: Aug. 9, 2017

(86) PCT No.: PCT/CN2017/096565
§ 371 (c)(1),
(2) Date: Jul. 22, 2019

(87) PCT Pub. No.: WO2018/133390
PCT Pub. Date: Jul. 26, 2018

(65) Prior Publication Data
US 2021/0080395 A1 Mar. 18, 2021

(30) Foreign Application Priority Data
Jan. 22, 2017 (CN) .......................... 201710045378.7

(51) Int. Cl.
*A61B 5/1172* (2016.01)
*G01N 21/64* (2006.01)

(52) U.S. Cl.
CPC ........ *G01N 21/6486* (2013.01); *A61B 5/1172* (2013.01); *G01N 2021/6491* (2013.01); *G01N 2021/6497* (2013.01)

(58) Field of Classification Search
CPC ............. A61B 5/1172; G01N 21/6486; G01N 2021/6491; G01N 2021/6497
See application file for complete search history.

(56) References Cited

U.S. PATENT DOCUMENTS 6,127,189 A 10/2000 Joullie et al.

FOREIGN PATENT DOCUMENTS

| CN | 102908149 A | 2/2013 |
|----|-------------|--------|
| CN | 103937033 A | 7/2014 |

(Continued)

OTHER PUBLICATIONS

D'elia et al., "Evaluation and Comparison of 1,2-indanedione and 1,8-diazafluoren-9-one Solutions for the Enhancement of Latent Fingerprints on Porous Surfaces," Forensic Science International, vol. 254, Jul. 30, 2015, 10 pages.

(Continued)

*Primary Examiner* — Mark R Gaworecki
(74) *Attorney, Agent, or Firm* — Hauptman Ham, LLP (57) ABSTRACT

A method for developing and extracting biological trace evidence comprises the following steps: (1) using a biological fluorescent development reagent to process a porous carrier so as to develop biological trace evidence on the porous carrier, wherein a raw material formulation of the biological fluorescent development reagent is, in percent by weight: 0.01%-0.5% of indanedione, 4%-10% of ethyl acetate, 0.5%-1.5% of glycerol, 5%-15.5% of pure alcohol, and 73.5%-90% of petroleum ether; and (2) extracting the biological trace evidence to obtain DNA information of the biological trace evidence. For crime investigators who need to extract DNA evidence, the method enables targeted extraction of physical evidence, thereby greatly reducing workload, and furthermore, the method can also be used to develop and extract obscure or trace evidence, such as a (Continued)

fingerprint on a garment, thereby greatly improving investigation efficiency.

20 Claims, 4 Drawing Sheets

(56) References Cited

FOREIGN PATENT DOCUMENTS

| CN | 104605860 A | 5/2015 |
|----|-------------|--------|
| CN | 106802292 A | 6/2017 |
| CN | 106841140 A | 6/2017 |

OTHER PUBLICATIONS

International Search Report dated Oct. 26, 2017, issued in corresponding International Patent Application No. PCT/CN20171096565, citing the above references.

Wang et al., Evaluation and Application of Ethanol as Carrier Solvent for 12-Indanedione(IDO) Fingermark Reagent, Journal of South-Central University for Nationalities (Nat. Sci. Edition), vol. 30, No. 3, Sep. 2011, 4 pages, with English Abstract.

Chen et al., "Latent Fingerprint Development on Thermal Paper Using Traditional Ninhydrin and 1,2-indanedione," Journal of Forensic Sciences, vol. 61, No. 1, Jan. 2016, 7 pages.

METHOD FOR DEVELOPING AND EXTRACTING BIOLOGICAL TRACE EVIDENCE

CROSS-REFERENCE TO RELATED APPLICATIONS

The present application is a National Phase of International Application Number PCT/CN2017/096565, filed Aug. 9, 2017, and claims the priority of China Application No. 201710045378.7, filed Jan. 22, 2017.

TECHNICAL FIELD OF THE INVENTION

The present disclosure relates to a method for developing and extracting biological trace evidence.

BACKGROUND OF THE INVENTION

In the field of criminal evidence reconnaissance, it is necessary to discover and obtain criminal evidences left by suspects, including fingerprint evidence, palmprint evidence, and trace evidence that can reflect DNA characteristics, thereby constructing an evidence chain of criminal facts and laying a legal evidence basis for punishing crimes. The existing criminal investigation means for the evidence collection of the physical evidence mainly includes checking fingerprints and checking DNA.

Checking the fingerprint only needs to take a picture and upload it to a computer, then compare with the fingerprints of the database and screen via the computer to find the suspect. However, some porous carriers, such as fabrics, are made by crossing, sintering and connecting some fine flexible slender objects, and therefore, although the fingerprint can be developed on the fabric, the line in the fingerprint is not continuous after the fingerprint is enlarged, and many breakpoints appear. Therefore, comparing the fingerprint photo on the fabric with the fingerprints of the database, many suspects may appear, or there may be no suspects, but these suspects may not be the real suspect, making it difficult to obtain evidence.

The existing method of checking DNA is using blue light at the crime scene, and cutting off the portion with blood or other obvious traces of the clothes with blood or other traces (such as semen), taking it back to the laboratory for DNA extraction, and then comparing with the database and screening, however the workload is huge, and it is difficult to find traces that are not obvious or trace, which makes it difficult to obtain evidence.

SUMMARY OF THE INVENTION

The technical problem to be solved by the present disclosure is to provide a method for developing and extracting biological trace evidence.

To solve the above technical problem, the present disclosure employs the following technical solution:
a method for developing and extracting biological trace evidence, comprises following steps:
(1) using a biological fluorescent development reagent to process a porous carrier so as to develop biological trace evidence on the porous carrier, wherein a raw material formulation of the biological fluorescent development reagent is, in percent by weight: 0.01%-0.5% of indanedione, 4%-10% of ethyl acetate, 0.5%-1.5% of glycerol, 5%-15.5% of pure alcohol, and 73.5%-90% of petroleum ether;

(2) extracting the biological trace evidence to obtain DNA information of the biological trace evidence.

Further, the step (1) is specifically implemented as follows: immersing the porous carrier in the biological fluorescent development reagent or spraying the biological fluorescent development reagent on the porous carrier, drying the porous carrier in an environment having a relative humidity of less than 40% at a temperature of 50° C.-120° C., irradiating the dried porous carrier with a laser having a wavelength of 532 nm and a full width at half-maximum of less than 1 nm, controlling a surface of the porous carrier with an illuminance of over 300,000 lux, and using a cut-off filter under 540 nm to develop the biological trace evidence on the porous carrier.

More further, before immersing in the biological fluorescent development reagent or spraying the biological fluorescent development reagent, a moisture content of the porous carrier is controlled to be less than 8%.

More further preferably, before immersing in the biological fluorescent development reagent or spraying the biological fluorescent development reagent, a moisture content of the porous carrier is controlled to be 6-7%.

More further, the porous carrier is dried in an environment having a relative humidity of less than 30% at a temperature of 50° C.-90° C.

More further, when immersing the porous carrier in the biological fluorescent development reagent, immersing time is controlled to be 5-10 sec.

In the present implementations, a cut-off filter under 540 nm refers to a cut-off filter that allows only light waves of or above 540 nm to pass through, and other light waves cannot pass.

Further, the porous carrier comprises fabric. The fabric includes, but not limited to, cloth, specifically cotton cloth.

More further, the raw material formulation of the biological fluorescent development reagent is, 0.05%-0.25% of indanedione, 4%-10% of ethyl acetate, 0.5%-1.5% of glycerol, 5%-15.5% of pure alcohol, and 74%-90% of petroleum ether.

More further preferably, the raw material formulation of the biological fluorescent development reagent is, 0.1%-0.2% of indanedione, 4%-10% of ethyl acetate, 0.5%-1.5% of glycerol, 8%-15% of pure alcohol, and 75%-85% of petroleum ether.

In the present disclosure, the biological trace evidence comprises a handprint.

In this implementation, the handprint refers to a fingerprint or a palmprint.

In the present disclosure, pure alcohol means >99.7% absolute ethanol, $C_2H_5OH$.

Preferably, a method for preparing the biological fluorescent development reagent comprises following steps:
(a) dissolving glycerin in pure alcohol to obtain a solution 1;
(b) dissolving indanedione in ethyl acetate to obtain a solution 2;
(c) mixing the solution 1 obtained in the step (a) and the solution 2 obtained in the step (b), adding petroleum ether, and uniformly stirring the mixture to give the biological fluorescent development reagent.

Preferably, the developing and extracting method further comprises cutting off a portion of the porous carrier where the biological trace evidence is developed, and then performing the step (2).

The present disclosure provides an alternative technical solution, which specifically is a method for developing and extracting biological trace evidence comprising following steps:

(1) using a biological fluorescent development reagent to process a porous carrier so as to develop biological trace evidence on the porous carrier, wherein a raw material formulation of the biological fluorescent development reagent is indanedione, ethyl acetate, glycerol, pure alcohol and petroleum ether; wherein, in volume ratio, ethyl acetate: glycerol:pure alcohol:petroleum ether=(3-8):(0.3-0.8):(5-15):(60-80); when preparing, indanedione is dissolved in ethyl acetate at a mass concentration of 0.0025-0.1 g/mL;

(2) extracting the biological trace evidence to obtain DNA information of the biological trace evidence.

Preferably, when preparing, indanedione is dissolved in ethyl acetate at a mass concentration of 0.00625-0.05 g/mL.

Preferably, the raw material formulation of the biological fluorescent development reagent is, 0.05-0.15 g of indanedione, 3-8 mL of ethyl acetate, 0.3-0.8 mL of glycerol, 5-15 mL of pure alcohol, and 60-80 mL of petroleum ether.

Due to the implementation of the above technical solution, the present disclosure has the following advantages over the prior art:

In the method for developing and extracting biological trace evidence of the present disclosure, a biological fluorescent development reagent is used to develop biological trace evidence, and then DNA information of the biological trace evidence is extracted, and the extracted DNA is compared and screened to finally find a suspect. For crime investigators who need to extract DNA evidence, the method enables targeted extraction of physical evidence, thereby greatly reducing workload, and furthermore, the method can also be used to develop and extract obscure or trace evidence, such as a fingerprint on a garment, thereby greatly improving investigation efficiency.

The biological fluorescent development reagent used in the method of the present disclosure produces no obvious acid odor, and thus does not cause an unpleasant experience to an operator.

DETAILED DESCRIPTION OF EXEMPLARY EMBODIMENTS

In the following, the present disclosure is further explained in detail combining with the specific embodiments, but not limited to these embodiments.

Embodiment 1

This embodiment provides a method for developing and extracting biological trace evidence, the sample was a sweat fingerprint trace (the lines are intermittent) on a white cotton cloth, and a formulation of a biological fluorescent development reagent used in this method was: indanedione 0.10 g; ethyl acetate 5 mL; glycerol 0.5 mL; pure alcohol 10 mL; petroleum ether 75 mL.

The method for developing and extracting comprises the following steps:

(1) The moisture content of the cotton cloth was controlled by drying to be less than 7%;

(2) In an environment of 25° C. and a relative humidity of 60%, mL 0.5 mL glycerol was added into 10 mL pure alcohol, and the solution was thoroughly stirred and dissolved to prepare a solution 1; 0.10 g indanedione was sufficiently dissolved in 5 mL ethyl acetate to prepare a solution 2, and the mass concentration of indanedione was 0.02 g/mL; the solution 1 and the solution 2 were mixed, then 75 mL petroleum ether was added, stirred and dissolved, and formulated into the fluorescent development reagent, and the fluorescent development reagent was used after it was ready, and if storage was required, it was stored in a brown light-proof bottle at normal temperature 25° C. or below 25° C. and used up within 30 days.

(3) The cotton cloth was immersed in the fluorescent development reagent for 8 sec.

(4) After the attached reagent on the soaked cotton cloth was volatilized under the ambient temperature (25° C.), the cotton cloth was dried in an environment with a relative humidity of less than 30% and a temperature of 60° C.-65° C. for 10 min.

Figure 1:
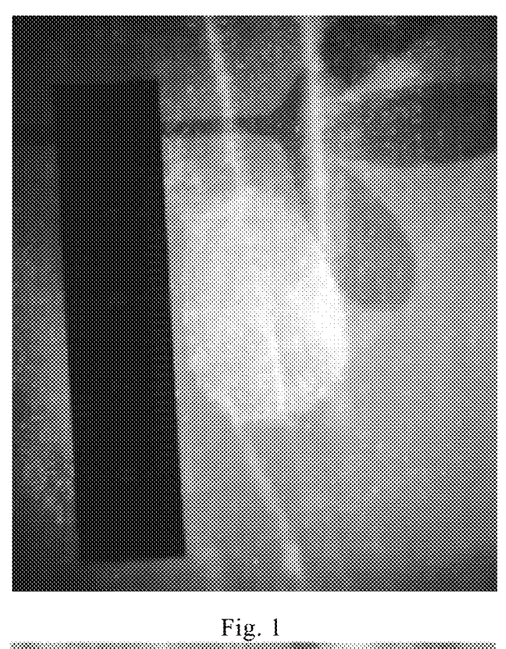
FIG. 1 is a photo of a fingerprint of Embodiment 1.
Figure 2:
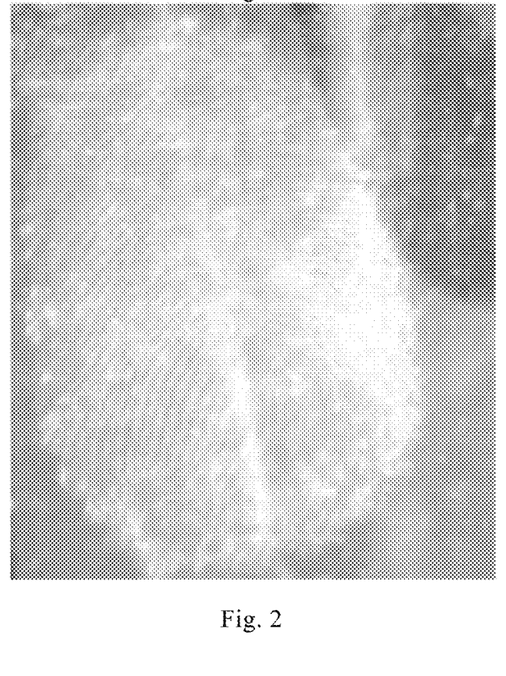
FIG. 2 is an enlarged photo of the fingerprint of Embodiment 1.

(5) The dried cotton cloth was irradiated with a laser having a wavelength of 532 nm and a full width at half-maximum of less than 1 nm, an illuminance of 300,000 lux was controlled to be formed on a surface of the cotton cloth, and the fingerprint as shown in FIG. 1 was obtained by photographing under a 540 nm filter, and see FIG. 2 for an enlarged fingerprint map.

(6) A portion of the cotton cloth with the fingerprint was cut off by scissors.

(7) The fingerprint trace on the cut cotton cloth was extracted to obtain DNA information of the fingerprint.

Figure 8:
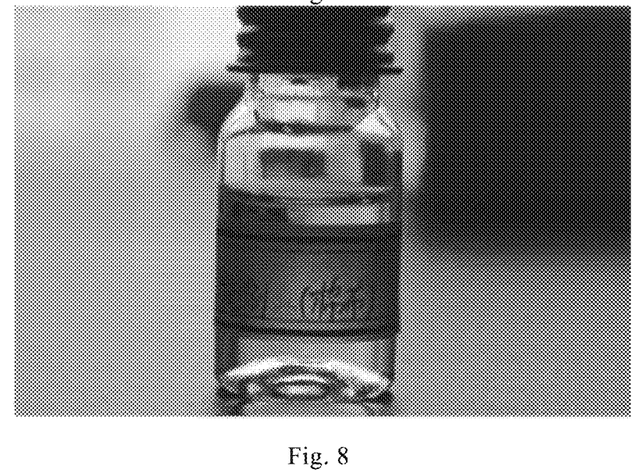
FIG. 8 is a state diagram of a reagent used in Embodiment 1 after being stored for 30 days.

The state of the biological fluorescent development reagent used in the method of this embodiment after 30 days of storage is shown in FIG. 8, and it was found that there was no crystallization or other variation appeared in the reagent.

Embodiment 2

This embodiment provides a method for developing and extracting biological trace evidence, the sample was a sweat fingerprint trace (the lines are intermittent) on a red cotton cloth, and a formulation of a biological fluorescent development reagent used in this method was: indanedione 0.11 g; ethyl acetate 5 mL; glycerol 0.5 mL; pure alcohol 10 mL; petroleum ether 75 mL.

The method for developing and extracting comprises the following steps:

(1) The moisture content of the cotton cloth was controlled by drying to be less than 7%.

(2) In an environment of 25° C. and a relative humidity of 60%, mL 0.5 mL glycerol was added into 10 mL pure alcohol, and the solution was thoroughly stirred and dissolved to prepare a solution 1; 0.11 g indanedione was sufficiently dissolved in 5 mL ethyl acetate to prepare a solution 2, and the mass concentration of indanedione was 0.022 g/mL; the solution 1 and the solution 2 were mixed, then 75 mL petroleum ether was added, stirred and dissolved, and formulated into the fluorescent development reagent, and the fluorescent development reagent was used after it was ready, and if storage was required, it was stored in a brown light-proof bottle at normal temperature 25° C. or below 25° C. and used up within 30 days.

(3) The cotton cloth was immersed in the fluorescent development reagent for 8 sec.

(4) After the attached reagent on the soaked cotton cloth volatilized under the ambient temperature (25° C.), the cotton cloth was dried in an environment with a relative humidity of less than 30% and a temperature of 60° C.-65° C. for 10 min.

Figure 3:
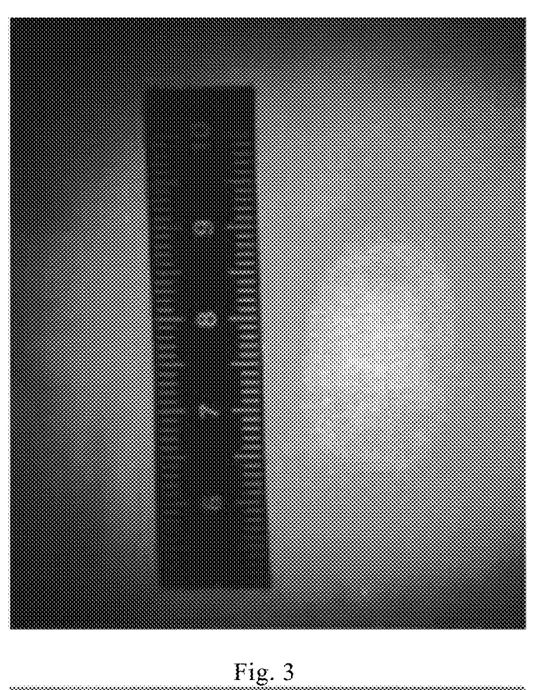
FIG. 3 is a photo of a fingerprint of Embodiment 2.
Figure 4:
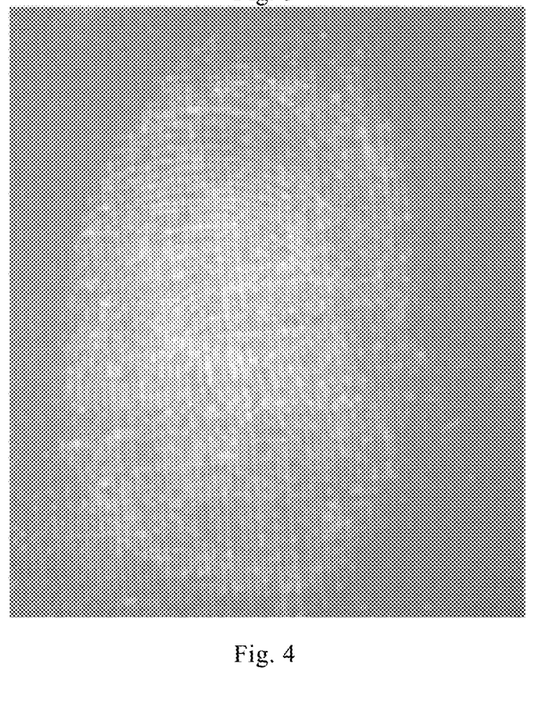
FIG. 4 is an enlarged photo of the fingerprint of Embodiment 2.

(5) The dried cotton cloth was irradiated with a laser having a wavelength of 532 nm and a full width at half-maximum of less than 1 nm, an illuminance of 300,000 lux was controlled to be formed on a surface of the cotton cloth, and the fingerprint as shown in FIG. 3 was obtained by photographing under a 540 nm filter, and see FIG. 4 for an enlarged fingerprint map.

(6) A portion of the cotton cloth with the fingerprint was cut off by scissors.

(7) The fingerprint trace on the cut cotton cloth was extracted to obtain DNA information of the fingerprint.

Embodiment 3

This embodiment provides a method for developing and extracting biological trace evidence, the sample was a sweat fingerprint trace (the lines are intermittent) on a blue cotton cloth, and a formulation of a biological fluorescent development reagent used in this method was: indanedione 0.11 g; ethyl acetate 5 mL; glycerol 0.5 mL; pure alcohol 10 mL; petroleum ether 75 mL.

The method for developing and extracting comprises the following steps:

(1) The moisture content of the cotton cloth was controlled by drying to be less than 7%;

(2) In an environment of 25° C. and a relative humidity of 60%, mL 0.5 mL glycerol was added into 10 mL pure alcohol, and the solution was thoroughly stirred and dissolved to prepare a solution 1; 0.11 g indanedione was sufficiently dissolved in 5 mL ethyl acetate to prepare a solution 2, and the mass concentration of indanedione was 0.022 g/mL; the solution 1 and the solution 2 were mixed, then 75 mL of petroleum ether was added, stirred and dissolved, and formulated into the fluorescent development reagent, and the fluorescent development reagent was used after it was ready, and if storage was required, it was stored in a brown light-proof bottle at normal temperature 25° C. or below 25° C. and used up within 30 days.

(3) The cotton cloth was immersed in the fluorescent development reagent for 8 sec.

(4) After the attached reagent on the soaked cotton cloth volatilized under the ambient temperature (25° C.), the cotton cloth was dried in an environment with a relative humidity of less than 30% and a temperature of 60° C.-65° C. for 10 min.

Figure 5:
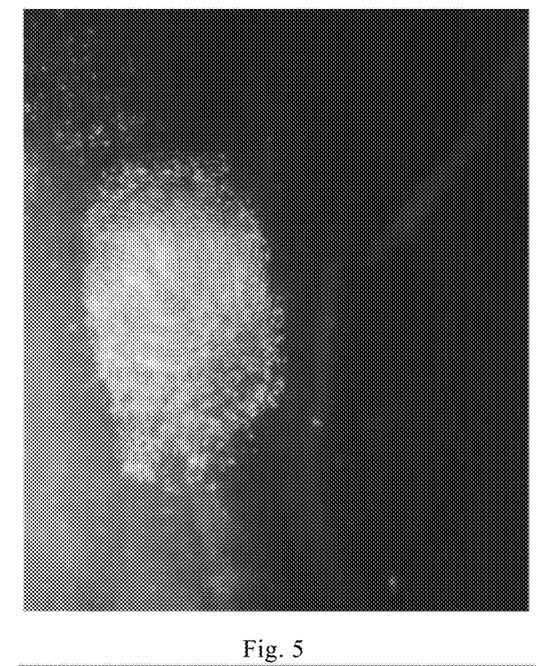
FIG. 5 is a photo of a fingerprint of Embodiment 3.
Figure 6:
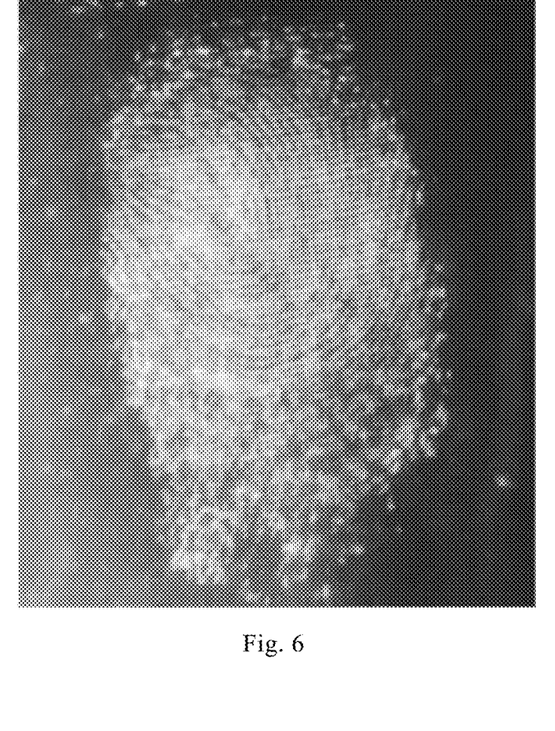
FIG. 6 is an enlarged photo of the fingerprint of Embodiment 3.

(5) The dried cotton cloth was irradiated with a laser having a wavelength of 532 nm and a full width at half-maximum of less than 1 nm, an illuminance of 300,000 lux was controlled to be formed on a surface of the cotton cloth, and the fingerprint as shown in FIG. 5 was obtained by photographing under a 540 nm filter, and see FIG. 6 for an enlarged fingerprint map.

(6) A portion of the cotton cloth with the fingerprint was cut off by scissors.

(7) The fingerprint trace on the cut cotton cloth was extracted to obtain DNA information of the fingerprint.

Embodiment 4

This embodiment provides a method for developing and extracting biological trace evidence, the sample was a sweat handprint scratch (the lines are incomplete) on a cotton cloth, and a formulation of a biological fluorescent development reagent used in this method was: indanedione 0.12 g; ethyl acetate 6 mL; glycerol 0.6 mL; pure alcohol 12 mL; petroleum ether 75 mL.

The method for developing and extracting comprises the following steps:

(1) The moisture content of the cotton cloth was controlled by drying to be less than 7%;

(2) In an environment of 25° C. and a relative humidity of 60%, 0.6 mL glycerol was added into 12 mL pure alcohol, and the solution was thoroughly stirred and dissolved to prepare a solution 1; 0.12 g indanedione was sufficiently dissolved in 6 mL of ethyl acetate to prepare a solution 2, and the mass concentration of indanedione was 0.02 g/mL; the solution 1 and the solution 2 were mixed, then 75 mL petroleum ether was added, stirred and dissolved, and formulated into the fluorescent development reagent, and the fluorescent development reagent was used after it was ready, and if storage was required, it was stored in a brown light-proof bottle at normal temperature 25° C. or below 25° C. and used up within 30 days.

(3) The cotton cloth was immersed in the fluorescent development reagent for 8 sec.

(4) After the attached reagent on the soaked cotton cloth was volatilized under the ambient temperature (25° C.), the cotton cloth was dried in an environment with a relative humidity of less than 30% and a temperature of 60° C.-65° C. for 10 min.

Figure 7:
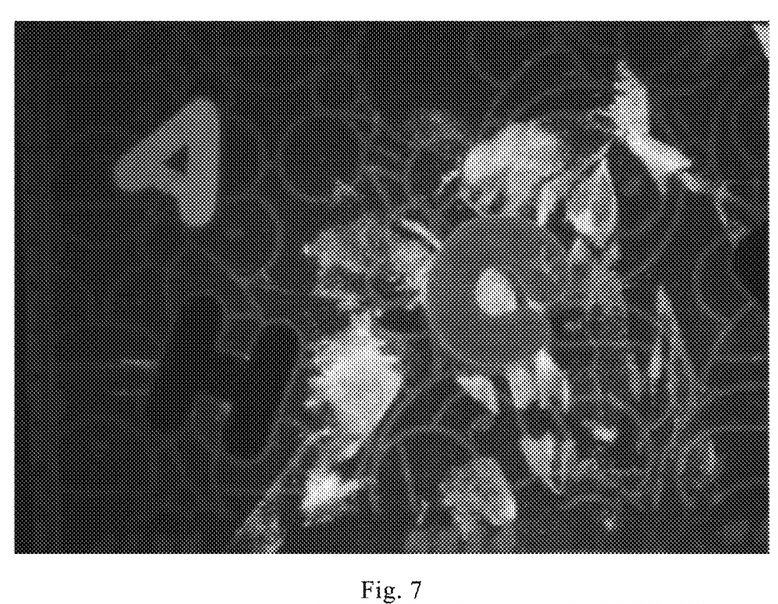
FIG. 7 is a photo of a handprint scratch of Embodiment 4.

(5) The dried cotton cloth was irradiated with a laser having a wavelength of 532 nm and a full width at half-maximum of less than 1 nm, an illuminance of 300,000 lux was controlled to be formed on a surface of the cotton cloth, and the handprint scratch was obtained by photographing under a 540 nm filter, see FIG. 7.

(6) A portion of the cotton cloth with the handprint scratch was cut off by scissors.

(7) The handprint scratch trace on the cut cotton cloth was extracted to obtain DNA information of the handprint scratch.

In the actual criminal investigation, it is only necessary to cut off the carrier with fingerprints or scratches, and take the cut carrier back to the laboratory to extract DNA of the fingerprints or scratches, which has good pertinence, and which not only greatly reduces the workload, but also greatly reduces the difficulty of obtaining evidence and improves the efficiency of cracking criminal cases. Moreover, for criminal investigators of DNA forensics, the method adopted by the present disclosure greatly reduces the difficulty of DNA forensics.

The method of the present disclosure can also spray the biological fluorescent development reagent onto a carrier with fingerprints or scratches by a manner of spraying to develop fingerprints or scratches on the carrier.

From the above, the method of the present disclosure has the following advantages:

In the method for developing and extracting biological trace evidence of the present disclosure, a biological fluorescent development reagent is used to develop biological trace evidence, and then DNA information of the biological trace evidence is extracted, and the extracted DNA is compared and screened to finally find a suspect. For crime investigators who need to extract DNA evidence, the method enables targeted extraction of physical evidence, thereby greatly reducing workload, and furthermore, the method can also be used to develop and extract some obscure evidences, such as a fingerprint on a garment, thereby not only greatly reducing the workload, but also greatly reducing the difficulty of obtaining evidence.

The biological fluorescent development reagent used in the method of the present disclosure produces no obvious acid odor, and thus does not cause an unpleasant experience to an operator.

Glycerol is used in the biological fluorescent development reagent used in the method of the present disclosure, and glycerol has a function of slow volatility, and therefore, when the spraying method is employed, the phenomenon that the precipitated crystals block the nozzle will not occur after spraying a plurality of times (four times or more).

The storage condition of the biological fluorescent development reagent of the present disclosure is widened, (more convenient for use), and the appearance of crystallization will not occur after storage at normal temperature (25° C.) for 30 days.

The biological fluorescent development reagent used in the present disclosure is very suitable for spraying, so after it is sprayed over the sample, the solvent can be volatilized very quickly, and the handprint can be quickly developed, which is very suitable for the requirement of rapid development.

The above detailed describes the present disclosure, is intended to make those skilled in the art being able to understand the present disclosure and thereby implement it, and should not be concluded to limit the protective scope of this disclosure. Any equivalent variations or modifications according to the essence of the present disclosure should be covered by the protective scope of the present disclosure.

What is claimed is:

1. A method for developing and extracting biological trace evidence, comprising following steps:
   (1) using a biological fluorescent development reagent to process a porous carrier so as to develop biological trace evidence on the porous carrier, wherein a raw material formulation of the biological fluorescent development reagent is, in percent by weight: 0.01%-0.5% of indanedione, 4%-10% of ethyl acetate, 0.5%-1.5% of glycerol, 5%-15.5% of pure alcohol, and 73.5%-90% of petroleum ether; and
   (2) extracting the biological trace evidence to obtain DNA information of the biological trace evidence.

2. The method for developing and extracting biological trace evidence according to claim 1, wherein the step (1) is specifically implemented as follows:
   immersing the porous carrier in the biological fluorescent development reagent or spraying the biological fluorescent development reagent on the porous carrier;
   drying the porous carrier in an environment having a relative humidity of less than 40% at a temperature of 50° C.-120° C.;
   irradiating the dried porous carrier with a laser having a wavelength of 532 nm and a full width at half-maximum of less than 1 nm;
   controlling a surface of the porous carrier with an illuminance of over 300,000 lux; and
   using a cut-off filter under 540 nm to develop the biological trace evidence on the porous carrier.

3. The method for developing and extracting biological trace evidence according to claim 2, wherein, before immersing in the biological fluorescent development reagent or spraying the biological fluorescent development reagent, a moisture content of the porous carrier is controlled to be less than 8%.

4. The method for developing and extracting biological trace evidence according to claim 2, wherein the porous carrier is dried in an environment having a relative humidity of less than 30% at a temperature of 50° C.-90° C.

5. The method for developing and extracting biological trace evidence according to claim 2, wherein, when immersing the porous carrier in the biological fluorescent development reagent, immersing time is controlled to be 5-10 sec.

6. The method for developing and extracting biological trace evidence according to claim 1, wherein the porous carrier comprises fabric.

7. The method for developing and extracting biological trace evidence according to claim 6, wherein the raw material formulation of the biological fluorescent development reagent is, 0.05%-0.25% of indanedione, 4%-10% of ethyl acetate, 0.5%-1.5% of glycerol, 5%-15.5% of pure alcohol, and 74%-90% of petroleum ether.

8. The method for developing and extracting biological trace evidence according to claim 1, wherein the biological trace evidence comprises a handprint.

9. The method for developing and extracting biological trace evidence according to claim 1, wherein, a method for preparing the biological fluorescent development reagent comprises following steps:
   (a) dissolving glycerin in pure alcohol to obtain a solution 1;
   (b) dissolving indanedione in ethyl acetate to obtain a solution 2; and
   (c) mixing the solution 1 obtained in the step (a) and the solution 2 obtained in the step (b), adding petroleum ether, and uniformly stirring the mixture to give the biological fluorescent development reagent.

10. The method for developing and extracting biological trace evidence according to claim 1, wherein, the developing and extracting method further comprises cutting off a portion of the porous carrier where the biological trace evidence is developed, and then performing the step (2).

11. A method for developing and extracting biological trace evidence, comprising following steps:
    (1) using a biological fluorescent development reagent to process a porous carrier so as to develop biological trace evidence on the porous carrier, wherein a raw material formulation of the biological fluorescent development reagent is indanedione, ethyl acetate, glycerol, pure alcohol and petroleum ether; wherein, in volume ratio, ethyl acetate:glycerol:pure alcohol:petroleum ether=(3-8):(0.3-0.8):(5-15):(60-80); when preparing, indanedione is dissolved in ethyl acetate at a mass concentration of 0.0025-0.1 g/mL; and
    (2) extracting the biological trace evidence to obtain DNA information of the biological trace evidence.

12. The method for developing and extracting biological trace evidence according to claim 11, wherein the step (1) is specifically implemented as follows:
    immersing the porous carrier in the biological fluorescent development reagent or spraying the biological fluorescent development reagent on the porous carrier;
    drying the porous carrier in an environment having a relative humidity of less than 40% at a temperature of 50° C.-120° C.;
    irradiating the dried porous carrier with a laser having a wavelength of 532 nm and a full width at half-maximum of less than 1 nm;
    controlling a surface of the porous carrier with an illuminance of over 300,000 lux; and
    using a cut-off filter under 540 nm to develop the biological trace evidence on the porous carrier.

13. The method for developing and extracting biological trace evidence according to claim 12, wherein, before immersing in the biological fluorescent development reagent or spraying the biological fluorescent development reagent, a moisture content of the porous carrier is controlled to be less than 8%.

14. The method for developing and extracting biological trace evidence according to claim 12, wherein the porous carrier is dried in an environment having a relative humidity of less than 30% at a temperature of 50° C.-90° C.

15. The method for developing and extracting biological trace evidence according to claim 12, wherein, when immersing the porous carrier in the biological fluorescent development reagent, immersing time is controlled to be 5-10 sec.

16. The method for developing and extracting biological trace evidence according to claim 11, wherein the porous carrier comprises fabric.

17. The method for developing and extracting biological trace evidence according to claim 16, wherein, when preparing, indanedione is dissolved in ethyl acetate at a mass concentration of 0.00625-0.05 g/mL.

18. The method for developing and extracting biological trace evidence according to claim 17, wherein the raw material formulation of the biological fluorescent development reagent is, 0.05-0.15 g of indanedione, 3-8 mL of ethyl acetate, 0.3-0.8 mL of glycerol, 5-15 mL of pure alcohol, and 60-80 mL of petroleum ether.

19. The method for developing and extracting biological trace evidence according to claim 11, wherein a method for preparing the biological fluorescent development reagent comprises following steps:
  (a) dissolving glycerin in pure alcohol to obtain a solution 1;
  (b) dissolving indanedione in ethyl acetate to obtain a solution 2; and
  (c) mixing the solution 1 obtained in the step (a) and the solution 2 obtained in the step (b), adding petroleum ether, and uniformly stirring the mixture to give the biological fluorescent development reagent.

20. The method for developing and extracting biological trace evidence according to claim 11, wherein, the developing and extracting method further comprises cutting off a portion of the porous carrier where the biological trace evidence is developed, and then performing the step (2).

* * * * *